(12) United States Patent
Hong et al.

(10) Patent No.: US 12,173,345 B2
(45) Date of Patent: Dec. 24, 2024

(54) KETOREDUCTASE MUTANT AND METHOD FOR PRODUCING CHIRAL ALCOHOLS

(71) Applicant: ASYMCHEM LABORATORIES (TIANJIN) CO., LTD., TEDA Tianjin (CN)

(72) Inventors: Hao Hong, Morrisville, NC (US); James Gage, Morrisville, NC (US); Yi Xiao, Tianjin (CN); Na Zhang, Tianjin (CN); Xuecheng Jiao, Tianjin (CN); Kejian Zhang, Tianjin (CN); Yiming Yang, Tianjin (CN)

(73) Assignee: ASYMCHEM LABORATORIES (TIANJIN) CO., LTD., Tianjin (CN)

( * ) Notice: Subject to any disclaimer, the term of this patent is extended or adjusted under 35 U.S.C. 154(b) by 501 days.

(21) Appl. No.: 17/618,724

(22) PCT Filed: Jun. 13, 2019

(86) PCT No.: PCT/CN2019/091068
§ 371 (c)(1),
(2) Date: Dec. 13, 2021

(87) PCT Pub. No.: WO2020/248186
PCT Pub. Date: Dec. 17, 2020

(65) Prior Publication Data
US 2023/0002795 A1  Jan. 5, 2023

(51) Int. Cl.
*C12P 7/22* (2006.01)
*C12N 9/04* (2006.01)
*C12N 15/70* (2006.01)

(52) U.S. Cl.
CPC .............. *C12P 7/22* (2013.01); *C12N 9/0006* (2013.01); *C12N 15/70* (2013.01); *C12Y 101/01184* (2013.01)

(58) Field of Classification Search
CPC ......... C12P 7/22; C12N 9/0006; C12N 15/70; C12Y 101/01184
See application file for complete search history.

(56) References Cited

U.S. PATENT DOCUMENTS

2009/0311762 A1* 12/2009 Tschentscher ....... C12N 9/0008
435/189

FOREIGN PATENT DOCUMENTS

| CN | 108048417 A | 5/2018 |
|---|---|---|
| CN | 109355265 A | 2/2019 |
| CN | 109468293 A | 3/2019 |
| CN | 109796434 A | 5/2019 |
| JP | 2007502124 A | 2/2007 |
| JP | 2010252657 A | 11/2010 |
| WO | 2006061137 A1 | 6/2006 |
| WO | 2018200214 A2 | 11/2018 |

OTHER PUBLICATIONS

CN108048417, May 2019, English translation (Espacenet) (Year: 2018).*
Honda K., et al., "Improvement of Operational Stability of Ogataea Minuta Carbonyl Reductase for Chiral Alcohol Production", Journal of Bioscience and Bioengineering, vol. 123, No. 6, Feb. 14, 2017.
International Search Report for corresponding application PCT/CN2019/091068 filed Jun. 13, 2019; Mail dated Mar. 6, 2020.
Jiashan CEN, et al., "Progress in Molecular Modification of Microbial Carbonyl Reductase", Chinese Journal of Bioprocess Engineering, vol. 15, No. 3, May 15, 2017.
European Search Report for corresponding application EP19932958; Mail date Jan. 10, 2023.

* cited by examiner

*Primary Examiner* — Soren Harward
*Assistant Examiner* — Naghmeh Nina Moazzami
(74) *Attorney, Agent, or Firm* — CANTOR COLBURN LLP

(57) ABSTRACT

Provided is a ketoreductase mutant and a method for producing chiral alcohol using the same. The ketoreductase mutant has a sequence with amino acid mutations in the sequence shown in SEQ ID NO:1. The mutation sites include at least one of the following positions: 6th position, 21st position, 42nd position, 58th position, 61st position, 76th position, 87th position, 94th position, 96th position, 108th position, 113th position, 117th position, 144th position, 146th position, 147th position, 149th position, 151st position, 152nd, 156th position, 165th position, 177th position, and 198th position.

20 Claims, No Drawings

Specification includes a Sequence Listing.

KETOREDUCTASE MUTANT AND METHOD FOR PRODUCING CHIRAL ALCOHOLS

CROSS-REFERENCES TO RELATED APPLICATION

The present application is a National Stage of International Patent Application No: PCT/CN2019/091068 filed on Jun. 13, 2019, titled "Ketoreductase Mutant and Method for Producing Chiral Alcohol", the entire content of which is incorporated in this application by reference.

SEQUENCE LISTING

The present application contains a Sequence Listing which has been submitted electronically in ASCII format and is hereby incorporated by reference in its entirety. Said ASCII copy is named_Sequence_Listing.txt and is 2.4 kilobytes in size, and contains 1 sequence SEQ ID NO:1, which is identical to the sequence listing filed in the corresponding international application No. PCT/CN2019/091068 filed on Jun. 13, 2019.

TECHNICAL FIELD

The present disclosure relates to the technical field of compound synthesis, and specifically relates to a ketoreductase mutant and a method for producing chiral alcohol.

BACKGROUND

Chiral alcohol widely exists in nature, and it is a constitutional unit of many important bioactive molecules, and is an important intermediate to synthesize natural products and chiral drugs. Lots of chiral drugs contain one or more chiral centers; different chiral drugs have significant differences in pharmacological activity, metabolic process, metabolic rate and toxicity. Usually, one enantiomer is effective, but another one is inefficient or invalid, and even toxic. Therefore, how to efficiently and stereoselectively construct a compound containing a chiral center is significant in medical research and development.

Ketoreductase (KRED) may be also called carbony-reductase with classification No. EC 1.1.1.184, and is usually used for reducing prochiral aldehyde or ketone, thus being prepared chiral alcohol. KRED can not only transform aldehyde or ketone substrates into corresponding alcohol products, but also can catalyze alcohol products for reverse reaction, that is, alcohol substrate is subjected to catalytic oxidation to obtain the corresponding aldehyde or ketone. The catalytic reaction of ketoreductase requires the participation of cofactors, including reduced nicotinamide adenine dinucleotide (NADH), reduced nicotinamide adenine dinucleotide phosphate (NADPH), oxidized nicotinamide adenine dinucleotide (NAD) or oxidized nicotinamide adenine dinucleotide phosphate (NADP).

Usually, the reduction reaction of aldehyde or ketone requires the participation of a reduced cofactor NADH or NADPH; while in actual reaction, an oxidized cofactor NAD or NADP will be added to regenerate reduced NADH or NADPH via a proper cofactor regeneration system. Common cofactor regeneration systems include glucose and glucose dehydrogenase, formate and hydrogenlyase, secondary alcohol and secondary alcohol dehydrogenase, phosphite and phosphorous acid dehydrogenase as well as other similar systems. Generally, the replacement of a coenzyme regeneration system will not substantively influence the functions of ketoreductase.

Many kinds of ketoreductase have been applied in commercialized production, but there is no ketoreductase for catalysis directed to some substrates, or the catalytic efficiency is very low. Therefore, researchers need to seek an enzyme having higher catalytic efficiency to some substrates.

SUMMARY

The present disclosure aims at providing a ketoreductase mutant and a method for producing chiral alcohol, thus improving the catalytic activity of ketoreductase.

To achieve the above objective, according to an aspect of the present disclosure, provided is a ketoreductase mutant. The ketoreductase mutant has a sequence with amino acid mutations in the sequence shown in SEQ ID NO:1. The mutation sites comprise at least one of the following positions: 6th position, 21st position, 42nd position, 58th position, 61st position, 76th position, 87th position, 94th position, 96th position, 108th position, 113th position, 117th position, 144th position, 146th position, 147th position, 149th position, 151st position, 152nd, 156th position, 165th position, 177th position, and 198th position, 199th position, 200th position, 201st position, 202nd position, 223rd position, 96th position, 237th position and 230th position.

Further, the amino acid sequence of the ketoreductase mutant is an amino acid sequence obtained by mutation occurred in the amino acid sequence as shown in SEQ ID NO: 1, and the mutation includes at least one of the following mutation sites: E144T, E144V, E144A, L152F, L152R, L152A, L152V, E201A and D202A; or an amino acid sequence of the ketoreductase mutant has the mutation site in the mutated amino acid sequence, and the amino acid sequence has more than 95% identity with the mutated amino acid sequence.

Further, the amino acid sequence of the ketoreductase mutant is an amino acid sequence obtained by mutation occurred in the amino acid sequence as shown in SEQ ID NO: 1, and the amino acid mutation includes E144A.

Further, the amino acid mutation includes L152F or L152Y.

Further, the amino acid mutation includes any one of the following mutation site combinations: E144A+L152R, E144A+L152A, E144A+L152V, E144A+E201A, E144A+D202A, E144A+L152W, E144A+L152M, E144A+L152L, E144A+L152K, E144A+L152T, E144A+L152P, E144A+L152C, E144A+L152H, E144A+L152Q, E144A+L152E, E144A+L152S, E144A+L152G, E144A+F152C+G6S, E144A+L152C+L198Q+E201G and E144A+L152C+L198Q+E201G+G6S.

Further, the amino acid mutation includes any one of the following mutation site combinations: E144A+L152F+A94E+S96M, E144A+L152F+A94S+S96Q, E144A+L152F+A94V, E144A+L152F+A94Y+S96E, E144A+L152F+A94S+S96N, E144A+L152F+A94S+S96R, E144A+L152F+A94A+S96E, E144A+L152F+A94Y+S96K, E144A+L152F+A94R+S96K, E144A+L152F+A94S+S96A, E144A+L152F+A94V+S96Q, E144A+L152F+A94A+S96G, E144A+L152F+A94S+S96T, E144A+L152F+S96E, E144A+L152F+A94Y+S96L, E144A+L152F+S96D, E144A+L152F+A94E+S96A, E144A+L152F+A94T+S96Y, E144A+L152F+A94S, E144A+L152F+A94E+S96C, E144A+L152F+L198V, E144A+L152F+L198V+E201C, E144A+L152F+L198I+

E201I, E144A+L152F+L198V+E201A, E144A+L152F+ L198V+E201N, E144A+L152F+L198V+E201L, E144A+ L152F+L198Q+E201G, E144A+L152F+L198V+E201S, E144A+L152F+L198H+E201G, E144A+L152F+L198I+ E201V, E144A+L152F+L198V+E201G, E144A+L152F+ L198Y+E201L, E144A+L152F+L198V+E201F, E144A+ L152F+L198S+E201Y, E144A+L152F+G6S, E144A+ L152F+R108H, E144A+L152F+G117S, E144A+L152F+ I223V, E144A+L152F+G6S+R108H, E144A+L152F+ G117S+G6S, E144A+L152F+G117S+I223V, E144A+ L152F+I223V+G6S, E144A+L152F+I223V+R108H, E144A+L152F+R108H+G117S, E144A+L152F+G117S+ G6S, E144A+L152F+G117S+I223V+G6S, E144A+ L152F+G117S+I223V+R108H, E144A+L152F+L198Q+ E201G+G6S, E144A+F152Y+G6S, E144A+L152Y+ L198Q+E201G, E144A+L152Y+L198Q+E201G+G6S, E144A+L152Y+L198Q+E201G+G6S+L146V+I147A, E144A+L152Y+L198Q+E201G+G6S+L146Q+I147R, E144A+L152Y+L198Q+E201G+G6S+L146L+I147L, E144A+L152Y+L198Q+E201G+G6S+L146V+I147T, E144A+L152Y+L198Q+E201G+G6S+L146C+I147V, E144A+L152Y+L198Q+E201G+G6S+L146L+I147R, E144A+L152Y+L198Q+E201G+G6S+L146G+I147V, E144A+L152Y+L198Q+E201G+G6S+L146L+I147R, E144A+L152Y+L198Q+E201G+G6S+L146H+I147T, E144A+L152Y+L198Q+E201G+G6S+L146L+I147V, E144A+L152Y+L198Q+E201G+G6S+L146N+I147T, E144A+L152Y+L198Q+E201G+G6S+L146Q+I147V, E144A+L152Y+L198Q+E201G+G6S+L146T+I147V, E144A+L152Y+L198Q+E201G+G6S+L146D+I147V, E144A+L152Y+L198Q+E201G+G6S+L146L+I147T, E144A+L152Y+L198Q+E201G+G6S+L146W+I147V, E144A+L152Y+L198Q+E201G+G6S+L146W+I147C, E144A+L152Y+L198Q+E201G+G6S+L146M+I147A, E144A+L152Y+L198Q+E201G+G6S+L146M+I147S, E144A+L152Y+L198Q+E201G+G6S+L146S+I147V, E144A+L152Y+L198Q+E201G+G6S+L146I+I147A, E144A+L152Y+L198Q+E201G+G6S+L146I+I147D, E144A+L152Y+L198Q+E201G+G6S+L146A+I147V, E144A+L152Y+L198Q+E201G+G6S+L146M+I147V, E144A+L152F+L198Q+E201G+G6S+G148G+D149V, E144A+L152Y+L198Q+E201G+G6S+L146M+I147V+ D42E, E144A+L152Y+L198Q+E201G+G6S+L146M+ I147V+D149I, E144A+L152Y+L198Q+E201G+G6S+ L146M+I147V+M151R, E144A+L152Y+L198Q+E201G+ G6S+L146M+I147V+D42E+T199V+K200R, E144A+ L152Y+L198Q+E201G+G6S+L146M+I147V+D42E+ T199V, E144A+L152Y+L198Q+E201G+G6S+L146M+ I147V+D42E+T199V+Q76L, E144A+L152Y+L198Q+ E201G+G6S+L146M+I147V+D42E+T199V+G177D, E144A+L152Y+L198Q+E201G+G6S+L146M+I147V+ D42E+T199V+S96N+I113F, E144A+L152Y+L198Q+ E201G+G6S+L146M+I147V+D42E+T199V+N156S+ K237E, E144A+L152Y+L198Q+E201G+G6S+L146M+ I147V+D42E+T199V+F165Y+K200H, E144A+L152Y+ L198Q+E201G+G6S+L146M+I147V+D42E+T199V+ S96N+N156S, E144A+L152Y+L198Q+E201G+G6S+ L146M+I147V+D42E+T199V+K200H, E144A+L152Y+ L198Q+E201G+G6S+L146M+I147V+D42E+T199V+ K61E+N156S, E144A+L152Y+L198Q+E201G+G6S+ L146M+I147V+D42E+T199V+A21V+A58T+S96N, E144A+L152Y+L198Q+E201G+G6S+L146M+I147V+ D42E+T199V+G177D+A203V, E144A+L152Y+L198Q+ E201G+G6S+L146M+I147V+D42E+T199V+A87V and E144A+L152Y+L198Q+E201G+G6S+L146M+I147V+ D42E+T199V+M146K+Y230F. According to another aspect of the present disclosure, provided is a DNA molecule. The DNA molecule encodes the any one of the above ketoreductase mutants.

According to a further aspect of the present disclosure, provided is a recombinant plasmid. The recombinant plasmid contains any one of the above DNA molecules.

Further, the recombinant plasmid is pET-22a(+), pET-22b (+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a (+), pET-25b(+), pET-26b(+), pET-27b(+), pET-28a(+), pET-29a(+), pET-30a(+), pET-31b(+), pET-32a(+), pET-35b (+), pET-38b(+), pET-39b(+), pET-40b(+), pET-41a(+), pET-41b(+), pET-42a(+), pET-43a(+), pET-43b(+), pET-44a (+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

According to a further aspect of the present disclosure, provided is a host cell. The host cell contains any one of the above recombinant plasmids.

Further, the host cell includes prokaryotic cell or eukaryotic cell, preferably, the prokaryotic cell is *Escherichia coli*.

According to a further aspect of the present disclosure, provided is a method for producing chiral alcohol. The method includes a step of performing a reduction reaction on a chiral ketones compound to produce the chiral alcohol catalyzed by ketoreductase, wherein the ketoreductase is any one of the above ketoreductase mutants.

Further, the prochiral ketone compound has the following structural formula

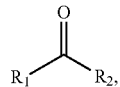

wherein $R_1$ and $R_2$ respectively independently are alkyl, cycloalkyl, aryl or heteroaryl, or the $R_1$ and the $R_2$ form a heterocyclyl, a carbocycle group or the heteroaryl with carbon on a carbonyl together, a heteroatom in the heterocyclyl and the heteroaryl is respectively independently selected from at least one of nitrogen, oxygen and sulfur, an aryl in the aryl, a heteroaryl in the heteroaryl, a carbocycle group in the carbocycle group or a heterocyclyl in the heterocyclyl are respectively independently unsubstituted or substituted by at least one group of halogen, alkoxy or alkyl;

the $R_1$ and the $R_2$ respectively and independently are $C_1$-$C_8$ alkyl, $C_5$-$C_{10}$ cycloalkyl, $C_5$-$C_{10}$ aryl or $C_5$-$C_{10}$ heteroaryl, or the $R_1$ and the $R_2$ form a $C_5$-$C_{10}$ heterocyclyl, a $C_5$-$C_{10}$ carbocycle group or the $C_5$-$C_{10}$ heteroaryl with the carbon on the carbonyl together, a heteroatom in the $C_5$-$C_{10}$ heterocyclyl and the $C_5$-$C_{10}$ heteroaryl is respectively independently selected from at least one of nitrogen, oxygen or sulfur, an aryl in the $C_5$-$C_{10}$ aryl, a heteroaryl in the $C_5$-$C_{10}$ heteroaryl, a carbocycle group in the $C_5$-$C_{10}$ carbocycle group or a heterocyclyl in the $C_5$-$C_{10}$ heterocyclyl are respectively independently unsubstituted or substituted by at least one group of halogen, alkoxy or alkyl;

preferably, a structure of the ketones compound is

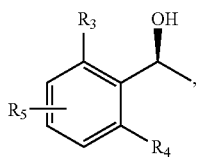

wherein $R_3$ is H, F, Cl, Br or $CH_3$, $R_4$ is H, F, Cl, Br or $CH_3$, and $R_5$ is H, F, Cl, Br, $CH_3$, $OCH_3$ or $CH_2CH_3$; and more preferably, the ketones compound is

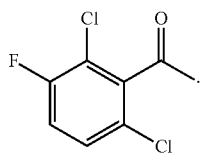

Further, a reaction system for performing the reduction reaction on the ketones compound to produce the chiral alcohol catalyzed by the ketoreductase further includes coenzyme, a coenzyme regeneration system and buffer.

Further, the ketone compound in the reaction system has a concentration of 1 g/L-200 g/L.

Further, the reaction system has a pH value of 5-9; and the reaction system has a reaction temperature of 4-60° C.

Further, the coenzyme is NADH.

Further, the coenzyme regeneration system includes: isopropanol, coenzyme $NAD^+$ and ketoreductase.

Further, the buffer solution is a phosphate buffer solution, Tris-hydrochloric acid buffer solution, barbital sodium-hydrochloric acid buffer solution or citric acid-sodium citrate buffer solution.

Based on the technical solution of the present disclosure, a ketone compound, as a raw material, is subjected to stereoselective reduction via ketoreductase to produce chiral alcohol efficiently, moreover, the selective isolation can be achieved, which reduces the production cost and post processing difficulty. Therefore, the present disclosure is suitable for expanding the industrial production of chiral alcohol.

DETAILED DESCRIPTION OF THE EMBODIMENTS

It should be indicated that examples in the present disclosure and features of the examples may be combined with each other. The present disclosure will be described specifically in combination with examples below.

Definitions

"Ketoreductase" and "KRED" may be used interchangeably in the present disclosure, and refer to a polypeptide which can reduce a ketone group to the corresponding alcohol. Specifically, the ketoreductase polypeptide of the present disclosure may stereoselectively reduce a ketone compound to the corresponding alcohol product. The polypeptide usually utilizes a cofactor, reduced nicotinamide adenine dinucleotide (NADH) or reduced nicotinamide adenine dinucleotide phosphate as a reductant. In this present disclosure, the ketoreductase includes natural (wild-type) ketoreductases and non-natural ketoreductase mutants produced via artificial process.

"Natural" or "wild-type" is relative to the "mutant", and refers to a form found in nature. For example, the natural or wild-type polypeptide or polynucleotide sequence is a sequence existing in a living body; it can be separated from a source in nature, and is not deliberately modified or changed by manual.

When the present disclosure relates to, for example, cell, nucleic acid or polypeptide "recombination", the cell, nucleic acid or polypeptide refers to the cell, nucleic acid or polypeptide which has been modified by a way of existence not existing in nature, or has a form of existence the same as that existing in nature, but is prepared or derived from a synthetic material and/or through the recombinant technology, or corresponds to a natural or an inherent form. Non-limiting examples include a gene expressing a form beyond an inherent (non-recombinant) form in cells or a recombinant cell expressing an inherent gene at different levels.

"Percentage of sequence identity" refers to an alignment between polynucleotides, and is determined by aligning two optimal alignment sequences via a cross-comparison window, where compared with a reference sequence, the portion of the polynucleotide sequence in the comparison window may include an addition or a deletion (namely, vacancy), thus being used for the best alignment of the two sequences. Percentage may be calculated as follows: the number of positions where there are same nucleic acid bases or amino acid residues in the two sequences is determined to generate the number of the match positions, then the number of the match positions divides the total number of the positions in the comparison window, and the result multiplies by 100 to obtain a percentage of sequence identity. Optionally, percentage may be calculated as follows: by determining the number of positions where there are same nucleic acid bases or amino acid residues in the two sequences, or nucleic acid bases or amino acid residues are aligned at vacancies, the number of the match positions is generated, then the number of the match positions divides the total number of the positions in the comparison window, and the result multiplies by 100 to obtain a percentage of sequence identity. "Reference sequence" refers to a designated sequence as a basis for the sequence comparison. Reference sequence may be a subset of a larger sequence, for example, a full-length gene or a segment of a polypeptide sequence.

Site-directed mutation: a desired change (usually a change representing a favorable direction), including addition, deletion, point mutation of a base, is introduced into a target DNA fragment (a genome or a plasmid is available) by means of polymerase chain reaction (PCR) and other methods. Site-directed mutation can rapidly and efficiently improve the characters and representation of the target protein expressed by DNA, and is a very useful means in gene research.

The method of introducing the site-directed mutation using a whole-plasmid PCR is simple and effective, and is a more commonly used method at present. A principle is that a pair of primers (forward and reverse) containing mutation sites are annealed with a template plasmid, and "circularly extended" by a polymerase. The so-called cyclic extension means that the polymerase extends the primer according to the template, and then returns to a 5'-end of the primer to be terminated after one round, and it undergoes circulation of repeated heating and annealing extension, this reaction is different from rolling circle amplification and does not form multiple tandem copies. Extension products of the forward and reverse primers are annealed and matched to form an open-circle plasmid with a nick. The extension product of Dpn I digestion, because the original template plasmid is derived from conventional *Escherichia coli*, is modified by dam methylation, and is fragmented because it is sensitive to Dpn I, the plasmid with a mutation sequence synthesized in vitro is not digested because it is not methylated, so it may be successfully transformed in the subsequent transformation, and a clone of the mutant plasmid may be obtained.

The mutation plasmid is transformed into a host cell for the induction expression of a target protein, then a crude enzyme is obtained by ultra-sonicating the cells.

Ketoreductase KRED derived from *Acetobacterpasteurianus* 386B may catalyze a target substrate to obtain a product, but has very low activity; 72 h after reaction, the conversion rate is still less than 0.1%. The present disclosure tries hard to improve the activity of ketoreductase KRED via orthogenesis to screen a ketoreductase mutant capable of being applied in industrial production and having a higher activity.

In this present disclosure, mutation sites are introduced into ketoreductase via whole-plasmid PCR, then detecting the activity of the mutants, thus selecting mutants having an improved activity. A mutation plasmid with a target gene is obtained with ketoreductase KRED as a template and pET-22b (+) as an expression vector by means of site-directed mutation.

The above obtained mutation plasmid is transformed into *Escherichia coli* cells for overexpression in *Escherichia coli*. A crude enzyme is obtained by ultra-sonicating the cells. Optimum conditions of the ketoreductase induction expression are: induced in 0.1 mM IPTG overnight at 25° C.

In a typical embodiment of the present disclosure, provided is a ketoreductase mutant. The ketoreductase mutant has a sequence with amino acid mutations in the sequence shown in SEQ ID NO: 1 (MARVAGKVAIVSGAAN-GIGKATAQLLAKEGAKVVIGDLKEEDGQ KAVAEI-KAAGGEAAFVKLNVTDEAAWKAAIGQTLKLYGRL-DIAVNNAGIAYSGSVEST SLEDWRRVQSINLDGVFLGTQVAIEAMKKSGGG-SIVNLSSIEGLIGDPMLAAYNASKGG VRLFTKSAALHCAKSGYKIRVNS-VHPGYIWTPMVAGLTKEDAAARQKLVDLHPIGHLG EPNDIAYGILYLASDESKFVTGSELVIDGGYTAQ); the mutation sites include at least one of the following sites: 6th position, 21st position, 42nd position, 58th position, 61st position, 76th position, 87th position, 94th position, 96th position, 108th position, 113th position, 117th position, 144th position, 146th position, 147th position, 149th position, 151st position, 152nd, 156th position, 165th position, 177th position, and 198th position, 199th position, 200th position, 201st position, 202nd position, 223rd position, 96th position, 237th position and 230th position. Preferably, the amino acid sequence of the ketoreductase mutant is an amino acid sequence obtained by mutation occurred in the amino acid sequence as shown in SEQ ID NO: 1, and the mutation includes at least one of the following mutation sites: E144T, E144V, E144A, L152F, L152R, L152A, L152V, E201A and D202A; or an amino acid sequence of the ketoreductase mutant has the mutation site in the mutated amino acid sequence, and the amino acid sequence has more than 95% identity with the mutated amino acid sequence. In some embodiments, the ketoreductase mutant has improved ketoreductase activity; the amino acid sequence has mutation sites in an amino acid sequence with mutations; and is 96%, 97%, 98%, or 99% identical with the amino acid sequence with mutations.

For the convenience of expression, the mutation in the present disclosure is denoted by a format of "primary amino acid-position-substituted amino acid", for example, "E144T" denotes that glutamic acid in the 144th position is mutated into threonine.

With a ketone compound as a raw material, the mutant obtained by above mutation in the present disclosure is subjected to stereoselective reduction to produce chiral alcohol efficiently, which reduces the production cost and post processing difficulty. Therefore, the mutant of the present disclosure is suitable for expanding the industrial production of chiral alcohol.

Preferably, the amino acid sequence of the ketoreductase mutant is an amino acid sequence obtained by mutation occurred in the amino acid sequence as shown in SEQ ID NO: 1, and the amino acid mutation includes E144A. A mutation merely in such a position of E144A may improve 10-50 times of the activity of ketoreductase. Further preferably, the amino acid mutation L152F or L152Y may greatly improve the activity of ketoreductase once again.

In a typical embodiment of the present disclosure, the amino acid mutation includes any one of the following mutation site combinations: E144A+L152R, E144A+L152A, E144A+L152V, E144A+E201A, E144A+D202A, E144A+L152W, E144A+L152M, E144A+L152L, E144A+L152K, E144A+L152T, E144A+L152P, E144A+L152C, E144A+L152H, E144A+L152Q, E144A+L152E, E144A+L152S, E144A+L152G, E144A+F152C+G6S, E144A+L152C+L198Q+E201G and E144A+L152C+L198Q+E201G+G6S.

more preferably, the amino acid mutation includes any one of the following mutation site combinations: E144A+L152F+A94E+S96M, E144A+L152F+A94S+S96Q, E144A+L152F+A94V, E144A+L152F+A94Y+S96E, E144A+L152F+A94S+S96N, E144A+L152F+A94S+S96R, E144A+L152F+A94A+S96E, E144A+L152F+A94Y+S96K, E144A+L152F+A94R+S96K, E144A+L152F+A94S+S96A, E144A+L152F+A94V+S96Q, E144A+L152F+A94A+S96G, E144A+L152F+A94S+S96T, E144A+L152F+S96E, E144A+L152F+A94Y+S96L, E144A+L152F+S96D, E144A+L152F+A94E+S96A, E144A+L152F+A94T+S96Y, E144A+L152F+A94S, E144A+L152F+A94E+S96C, E144A+L152F+L198V, E144A+L152F+L198V+E201C, E144A+L152F+L198I+E201I, E144A+L152F+L198V+E201A, E144A+L152F+L198V+E201N, E144A+L152F+L198V+E201L, E144A+L152F+L198Q+E201G, E144A+L152F+L198V+E201S, E144A+L152F+L198H+E201G, E144A+L152F+L198I+E201V, E144A+L152F+L198V+E201G, E144A+L152F+L198Y+E201L, E144A+L152F+L198V+E201F, E144A+L152F+L198S+E201Y, E144A+L152F+G6S, E144A+L152F+R108H, E144A+L152F+G117S, E144A+L152F+I223V, E144A+L152F+G6S+R108H, E144A+L152F+G117S+G6S, E144A+L152F+G117S+I223V, E144A+L152F+I223V+G6S, E144A+L152F+I223V+R108H, E144A+L152F+R108H+G117S, E144A+L152F+G117S+G6S, E144A+L152F+G117S+I223V+G6S, E144A+L152F+G117S+I223V+R108H, E144A+L152F+L198Q+E201G+G6S, E144A+F152Y+G6S, E144A+L152Y+L198Q+E201G, E144A+L152Y+L198Q+E201G+G6S, E144A+L152Y+L198Q+E201G+G6S+L146V+I147A, E144A+L152Y+L198Q+E201G+G6S+L146Q+I147R, E144A+L152Y+L198Q+E201G+G6S+L146L+I147L, E144A+L152Y+L198Q+E201G+G6S+L146V+I147T, E144A+L152Y+L198Q+E201G+G6S+L146C+I147V, E144A+L152Y+L198Q+E201G+G6S+L146L+I147R, E144A+L152Y+L198Q+E201G+G6S+L146G+I147V, E144A+L152Y+L198Q+E201G+G6S+L146L+I147R,
E144A+L152Y+L198Q+E201G+G6S+L146H+I147T,
E144A+L152Y+L198Q+E201G+G6S+L146L+I147V,
E144A+L152Y+L198Q+E201G+G6S+L146N+I147T,
E144A+L152Y+L198Q+E201G+G6S+L146Q+I147V,
E144A+L152Y+L198Q+E201G+G6S+L146T+I147V,
E144A+L152Y+L198Q+E201G+G6S+L146D+I147V,
E144A+L152Y+L198Q+E201G+G6S+L146L+I147T,
E144A+L152Y+L198Q+E201G+G6S+L146W+I147V,
E144A+L152Y+L198Q+E201G+G6S+L146W+I147C,
E144A+L152Y+L198Q+E201G+G6S+L146M+I147A,
E144A+L152Y+L198Q+E201G+G6S+L146M+I147S,
E144A+L152Y+L198Q+E201G+G6S+L146S+I147V,
E144A+L152Y+L198Q+E201G+G6S+L146I+I147A,
E144A+L152Y+L198Q+E201G+G6S+L146I+I147D,
E144A+L152Y+L198Q+E201G+G6S+L146A+I147V,
E144A+L152Y+L198Q+E201G+G6S+L146M+I147V,
E144A+L152F+L198Q+E201G+G6S+G148G+D149V,
E144A+L152Y+L198Q+E201G+G6S+L146M+I147V+D42E, E144A+L152Y+L198Q+E201G+G6S+L146M+I147V+D149I, E144A+L152Y+L198Q+E201G+G6S+L146M+I147V+M151R, E144A+L152Y+L198Q+E201G+G6S+L146M+I147V+D42E+K200R, E144A+L152Y+L198Q+E201G+G6S+L146M+I147V+D42E+T199V, E144A+L152Y+L198Q+E201G+G6S+L146M+I147V+D42E+T199V+Q76L, E144A+L152Y+L198Q+E201G+G6S+L146M+I147V+D42E+T199V+G177D, E144A+L152Y+L198Q+E201G+G6S+L146M+I147V+D42E+T199V+S96N+I113F, E144A+L152Y+L198Q+E201G+G6S+L146M+I147V+D42E+T199V+N156S+K237E, E144A+L152Y+L198Q+E201G+G6S+L146M+I147V+D42E+T199V+F165Y+K200H, E144A+L152Y+L198Q+E201G+G6S+L146M+I147V+D42E+T199V+S96N+N156S, E144A+L152Y+L198Q+E201G+G6S+L146M+I147V+D42E+T199V+K200H, E144A+L152Y+L198Q+E201G+G6S+L146M+I147V+D42E+T199V+K61E+N156S, E144A+L152Y+L198Q+E201G+G6S+L146M+I147V+D42E+T199V+A21V+A58T+S96N, E144A+L152Y+L198Q+E201G+G6S+L146M+I147V+D42E+T199V+G177D+A203V, E144A+L152Y+L198Q+E201G+G6S+L146M+I147V+D42E+T199V+A87V and E144A+L152Y+L198Q+E201G+G6S+L146M+I147V+D42E+T199V+M146K+Y230F.

According to a typical embodiment of the present disclosure, provided is a DNA molecule. The DNA molecule encodes the above ketoreductase mutant. The above ketoreductase encoded by the DNA molecule has very great vitality.

The above DNA molecule of the disclosure may also exist in the form of an "expression cassette". The "expression cassette" refers to a linear or circular nucleic acid molecule, includes DNA and RNA sequences that may direct the expression of a specific nucleotide sequence in an appropriate host cell. Generally speaking, it includes a promoter operatively linked with a target nucleotide, and it is optionally operatively linked with a termination signal and/or other regulatory elements. The expression cassette may also include a sequence required for proper translation of the nucleotide sequence. A coding region usually encodes the target protein, but also encodes a target functional RNA in sense or antisense direction, such as an antisense RNA or an untranslated RNA. The expression cassette containing the target polynucleotide sequence may be chimeric, it means that at least one of its components is heterologous to at least one of the other components thereof. The expression cassette may also be naturally existent, but obtained by efficient recombination for heterologous expression.

According to a typical embodiment of the present disclosure, provided is a recombinant plasmid. The recombinant plasmid contains any one of the above DNA molecules. The DNA molecule in the above recombinant plasmid is put in a proper position of the recombinant plasmid, such that the above DNA molecule can be correctly and smoothly replicated, transcribed or expressed.

Although a qualifier used in the disclosure to define the above DNA molecule is "containing", it does not mean that other sequences that are not related to its function may be arbitrarily added to both ends of the DNA sequence. It is known by those skilled in the art that in order to meet requirements of a recombination operation, it is necessary to add appropriate digestion sites of a restriction endonuclease at both ends of the DNA sequence, or additionally add a start codon, a stop codon and the like. Therefore, if closed-type expression is used to limit, these situations may not be truly covered.

A term "plasmid" used in the disclosure includes any plasmids, cosmids, bacteriophages or agrobacterium binary nucleic acid molecules in double-stranded or single-stranded linear or circular form, preferably a recombinant expression plasmid, or a prokaryotic expression plasmid or a eukaryotic expression plasmid, but preferably the prokaryotic expression plasmid. In some implementation schemes, the recombinant plasmid is selected from pET-22a(+), pET-22b(+), pET-3a(+), pET-3d(+), pET-11a(+), pET-12a(+), pET-14b (+), pET-15b(+), pET-16b(+), pET-17b(+), pET-19b(+), pET-20b(+), pET-21a(+), pET-23a(+), pET-23b(+), pET-24a (+), pET-25b(+), pET-26b(+), pET-27b(+), pET-28a(+), pET-29a(+), pET-30a(+), pET-31b(+), pET-32a(+), pET-35b (+), pET-38b(+), pET-39b(+), pET-40b(+), pET-41a(+), pET-41b(+), pET-42a(+), pET-43a(+), pET-43b(+), pET-44a (+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19. More preferably, the above recombinant plasmid is pET-22b(+).

According to a typical embodiment of the present disclosure, provided is a host cell, and the hose cell contains any one of the above recombinant plasmids. The host cell suitable for the present disclosure includes but not limited to prokaryotic cells, yeast or eukaryotic cells. Preferably, the prokaryotic cell is *Eubacterium*, for example, gram-negative bacterium or gram-positive bacterium. More preferably, the prokaryotic cell is an *Escherichia coli* BL21 cell or *Escherichia coli* DH5α competent cell.

According to a typical embodiment of the present disclosure, provided is a method for producing chiral alcohol. The method includes a step of performing a reduction reaction on a chiral ketones compound to produce the chiral alcohol catalyzed by ketoreductase, wherein the ketoreductase is any one of the above ketoreductase mutants. The above ketoreductase mutant of the present disclosure has great vitality; therefore, the chiral alcohol prepared by the ketoreductase mutant of the present disclosure may improve the reaction rate, increase substrate concentration, reduce dosage of enzyme and difficulty of the post processing.

In this present disclosure, the chiral ketone compound includes but not limited to the following structural formula

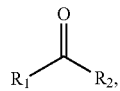

wherein $R_1$ and $R_2$ respectively independently are alkyl, cycloalkyl, aryl or heteroaryl, or the $R_1$ and the $R_2$ form a heterocyclyl, a carbocycle group or the heteroaryl with carbon on a carbonyl together, a heteroatom in the heterocyclyl and the heteroaryl is respectively independently selected from at least one of nitrogen, oxygen and sulfur, an aryl in the aryl, a heteroaryl in the heteroaryl, a carbocycle group in the carbocycle group or a heterocyclyl in the heterocyclyl are respectively independently unsubstituted or substituted by at least one group of halogen, alkoxy or alkyl;

the $R_1$ and the $R_2$ respectively and independently are $C_1$-$C_8$ alkyl, $C_5$-$C_{10}$ cycloalkyl, $C_5$-$C_{10}$ aryl or $C_5$-$C_{10}$ heteroaryl, or the $R_1$ and the $R_2$ form a $C_5$-$C_{10}$ heterocyclyl, a $C_5$-$C_{10}$ carbocycle group or the $C_5$-$C_{10}$ heteroaryl with the carbon on the carbonyl together, a heteroatom in the $C_5$-$C_{10}$ heterocyclyl and the $C_5$-$C_{10}$ heteroaryl is respectively independently selected from at least one of nitrogen, oxygen or sulfur, an aryl in the $C_5$-$C_{10}$ aryl, a heteroaryl in the $C_5$-$C_{10}$ heteroaryl, a carbocycle group in the $C_5$-$C_{10}$ carbocycle group or a heterocyclyl in the $C_5$-$C_{10}$ heterocyclyl are respectively independently unsubstituted or substituted by at least one group of halogen, alkoxy or alkyl; preferably, a structure of the ketones compound is

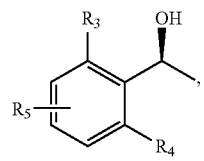

wherein $R_3$ is H, F, Cl, Br or $CH_3$, $R_4$ is H, F, Cl, Br or $CH_3$, and $R_5$ is H, F, Cl, Br, $CH_3$, $OCH_3$ or $CH_2CH_3$; and more preferably, the ketones compound is

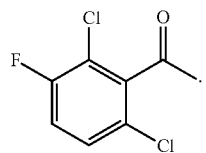

The above mentioned host cell of the present disclosure may be used for the expression and isolation of ketoreductase, or optionally, may directly used for transforming a ketone substrate to a chiral alcohol product. Preferably, the prokaryotic cell is *Escherichia coli*.

The above mentioned reduction reaction generally requires a cofactor, usually NADH or NADPH, and the reduction reaction may include a system for regenerating the cofactor, for example, D-glucose, coenzyme NAD$^+$ and glucose dehydrogenase GDH; formate compounds, coenzyme NAD$^+$ and formate dehydrogenase FDH; or isopropanol, coenzyme NAD$^+$ and alcohol dehydrogenase ADH. In some embodiments of using purified ketoreductase, such kind of cofactor and optionally, such kind of cofactor regeneration system is usually added to a reaction medium together with a substrate and ketoreductase. Similar to ketoreductase, any enzyme containing the cofactor regeneration system may be in a form of extract or lysate of such cells, or as a purified enzyme, may be added to a reaction mixture. In an embodiment of using cell extracts or cell lysates; the cell for producing extracts or lysates may contains a cofactor regeneration system only or a cofactor regeneration system and ketoreductase. In an embodiment of using a whole cell; the cell may contain a cofactor regeneration system and ketoreductase.

No matter what a whole cell, a cell extract or a purified ketoreductase is used, a single ketoreductase may be used, or optionally, a mixture of two or more ketoreductases may be used.

The reaction system that a chiral ketone compound is subjected to reduction reaction by ketoreductase to produce chiral alcohol may further include a coenzyme, a coenzyme regeneration system and a buffer solution.

The ketoreductase mutant of the present disclosure has a higher catalytic activity, and thus, can increase a concentration of a substrate and improve the production efficiency; the chiral ketone compound in the reaction system has a concentration of 1 g/L-200 g/L.

The reaction system has a pH value of 5-9, and a reaction temperature of 4-60° C.; the buffer solution is a phosphate buffer solution, Tris-hydrochloric acid buffer solution, barbital sodium-hydrochloric acid buffer solution or citric acid-sodium citrate buffer solution.

Beneficial effects of the present disclosure will be further described in combination with the examples below.

Example 1

10 mg 2,6-dichloro-3-fluoroacetophenone, 0.1 M PB (a phosphatic buffer solution) pH=7.0, 100 mg isopropanol, 0.1 mg NAD$^+$, and 10 mg ketoreductase (see Table 1) were added to a 10 mL reaction flask, and mixed evenly, and subjected to reaction for 40 h in a shaker at 30° C. and 200 rpm with a total volume of 1 mL. 2 mL ethyl acetate was added to the reaction system, after being mixed evenly, the sample reaction system was put to a 5 mL EP tube and centrifuged for 3 min at 12000 rpm. 15 μL supernatant was taken to a sample sending bottle, 1 mL ethyl acetate was added for HPLC detection, and the detection wavelength was 210 nm.

TABLE 1

| Mutant | Activity |
| --- | --- |
| WT | − |
| E144S | + |
| E144T | ++ |
| E144V | ++ |
| E144A | +++ |
| L152F | + |
| L152R | + |
| L152A | + |
| L152V | + |
| E201A | + |
| D202A | + |

The activity was denoted by a multiple improved relative to a parent, + denoted 1-5 times of improvement, ++ denoted 5-10 times of improvement, +++ denoted 10-50 times of improvement.

It can be seen from the result of Table 1 that the transformation effect of a single position mutant has been improved relative to the parent, but has not been up to the ideal result. Saturated mutations were combined to obtain a mutant having a synergistic effect between several mutation sites, and the composition of the amino acid of the mutant might be optimized.

In this example, a preparation method of an enzyme solution in high throughput screening: a 96-well plate was centrifuged to remove a supernatant medium, 200 μL enzymolysis solution (2 mg/mL lysozyme, 0.5 mg/mL polymyxin, pH=7.0) was added per well, and thermally insulated at 37° C. and lysed for 3 h.

In this example, the high throughput screening method was as follows: 200 μL reaction system: 2 mg 2,6-dichloro-3-fluoroacetophenone and 0.2 mg NAD⁺; 100 μL the enzyme solution was added at pH=7.0 and 30° C.

The screened mutant was subjected to shake-flask culture, and then subjected to amplification reaction.

Optimum conditions of the ketoreductase induction expression: induced in 0.1 mM IPTG overnight at 25° C.

Example 2

10 mg 2,6-dichloro-3-fluoroacetophenone, 0.1 M phosphatic buffer solution (pH=7.0), 100 mg isopropanol, 0.1 mg NAD⁺, and 10 mg ketoreductase (see details in Table 2) were added to a 10 mL reaction flask, and mixed evenly, and subjected to reaction for 40 h in a shaker at 30° C. and 200 rpm with a total volume of 1 mL. 2 mL ethyl acetate was added to the reaction system, after being mixed evenly, the reaction system was put into a 5 mL EP tube and centrifuged for 3 min at 12000 rpm. 15 μL supernatant was taken to a sample sending bottle, 1 mL ethyl acetate was added for HPLC detection, and the detection wavelength was 210 nm.

TABLE 2

| Mutant | Activity |
| --- | --- |
| WT | − |
| E144A + L152F | +++++ |
| E144A + L152R | +++++ |
| E144A + L152A | +++++ |
| E144A + L152V | +++++ |
| E144A + E201A | +++ |
| E144A + D202A | +++ |
| E144A + L152W | +++++ |
| E144A + L152M | ++++ |
| E144A + L152L | +++ |
| E144A + L152K | +++ |
| E144A + L152T | +++++ |
| E144A + L152P | +++++ |
| E144A + L152C | +++++ |
| E144A + L152H | +++++ |
| E144A + L152Y | ++++ |
| E144A + L152Q | ++++ |
| E144A + L152E | +++++ |
| E144A + L152S | +++++ |
| E144A + L152G | ++++ |
| E144A + L152F + A94E + S96M | +++++ |
| E144A + L152F + A94S + S96Q | +++++ |
| E144A + L152F + A94V | +++++ |
| E144A + L152F + A94Y + S96E | ++++++ |
| E144A + L152F + A94S + S96N | +++++ |
| E144A + L152F + A94S + S96R | +++++ |
| E144A + L152F + S96E | +++++ |
| E144A + L152F + A94Y + S96K | +++++ |
| E144A + L152F + A94R + S96K | +++++ |
| E144A + L152F + A94S + S96A | +++++ |
| E144A + L152F + A94V + S96Q | +++++ |
| E144A + L152F + S96G | +++++ |
| E144A + L152F + A94S + S96T | +++++ |
| E144A + L152F + S96E | +++++ |
| E144A + L152F + A94Y + S96L | +++++ |
| E144A + L152F + S96D | +++++ |
| E144A + L152F + A94E + S96A | +++++ |
| E144A + L152F + A94T + S96Y | +++++ |
| E144A + L152F + A94S | +++++ |
| E144A + L152F + A94E + S96C | ++++++ |
| E144A + L152F + L198V | ++++++ |
| E144A + L152F + L198V + E201C | ++++++ |
| E144A + L152F + L198I + E201I | ++++++ |
| E144A + L152F + L198V + E201A | ++++++ |
| E144A + L152F + L198V + E201N | ++++++ |

TABLE 2-continued

| Mutant | Activity |
| --- | --- |
| E144A + L152F + L198V + E201L | ++++++ |
| E144A + L152F + L198Q + E201G | ++++++ |
| E144A + L152F + L198V + E201S | ++++++ |
| E144A + L152F + L198H + E201G | ++++++ |
| E144A + L152F + L198I + E201V | ++++++ |
| E144A + L152F + L198V + E201G | ++++++ |
| E144A + L152F + L198Y + E201L | ++++++ |
| E144A + L152F + L198V + E201F | ++++++ |
| E144A + L152F + L198S + E201Y | ++++++ |
| E144A + L152F + G6S | +++++ |
| E144A + L152F + R108H | +++++ |
| E144A + L152F + G117S | +++++ |
| E144A + L152F + I223V | +++++ |
| E144A + L152F + G6S + R108H | +++++ |
| E144A + L152F + G117S + G6S | +++++ |
| E144A + L152F + G117S + I223V | +++++ |
| E144A + L152F + I223V + G6S | +++++ |
| E144A + L152F + I223V + R108H | +++++ |
| E144A + L152F + R108H + G117S | +++++ |
| E144A + L152F + G117S + G6S | +++++ |
| E144A + L152F + G117S + I223V + G6S | +++++ |
| E144A + L152F + G117S + I223V + R108H | +++++ |
| E144A + F152C + G6S | +++++ |
| E144A + F152Y + G6S | +++++ |
| E144A + L152F + L198Q + E201G + G6S | ++++++ |
| E144A + L152C + L198Q + E201G | +++++ |
| E144A + L152Y + L198Q + E201G | ++++++ |
| E144A + L152C + L198Q + E201G + G6S | +++++ |
| E144A + L152Y + L198Q + E201G + G6S | ++++++ |

The activity was denoted by a multiple improved relative to a parent, + denoted 1-5 times of improvement, ++ denoted 5-10 times of improvement, +++ denoted 10-50 times of improvement; ++++ denoted 50-100 times of improvement; +++++ denoted 100-1000 times of improvement; and ++++++ denoted more than 1000 times of improvement.

In industrial production, concentration of a substrate is very important to the control of the cost and three wastes; the higher the concentration of the reaction substrate is, the lower the cost is, and the less than generated wastes is. Based on the results in the early stage, the concentration of the substrate was increased 10 times, and mutation and screening were performed continuously, and results were shown in Table 2.

In this example, a preparation method of an enzyme solution in high throughput screening: a 96-well plate was centrifuged to remove a supernatant medium, 200 μL enzymolysis solution (2 mg/mL lysozyme, 0.5 mg/mL polymyxin, pH=7.0) was added per well, and thermally insulated at 37° C. and crushed for 3 h.

In this example, the high throughput screening method was as follows: 200 μL reaction system: 20 mg 2,6-dichloro-3-fluoroacetophenone and 2 mg NAD⁺; 100 μL the enzyme solution was added at pH=7.0 and 30° C.

The screened mutant was subjected to shake-flask culture, and then subjected to amplification reaction.

Optimum conditions of the ketoreductase induction expression: induced in 0.1 mM IPTG overnight at 25° C.

Example 3

1100 mg substrate, 2,6-dichloro-3-fluoroacetophenone, 0.1 M phosphatic buffer solution (pH=7.0), 100 mg isopropanol, 1 mg NAD⁺, and 10 mg ketoreductase (see Table 3) were added to a 10 mL reaction flask, and mixed evenly, and subjected to reaction for 40 h in a shaker at 30° C. and 200 rpm with a total volume of 1 mL. 2 mL ethyl acetate was added the reaction system, after being mixed evenly, the reaction system was put to a 5 mL EP tube and centrifuged for 3 min at 12000 rpm. 15 μL supernatant was taken to a sample sending bottle, 1 mL ethyl acetate was added for HPLC detection, and the detection wavelength was 210 nm.

TABLE 3

| Mutant | Activity |
| --- | --- |
| WT | — |
| E144A + L152Y + L198Q + E201 G + G6S + L146V + I147A | +++++ |
| E144A + L152Y + L198Q + E201 G + G6S + L146Q + I147R | +++++ |
| E144A + L152Y + L198Q + E201 G + G6S + I147L | +++++ |
| E144A + L152Y + L198Q + E201 G + G6S + L146V + I147T | +++++ |
| E144A + L152Y + L198Q + E201 G + G6S + L146C + I147V | +++++ |
| E144A + L152Y + L198Q + E201 G + G6S + I147R | ++++++ |
| E144A + L152Y + L198Q + E201 G + G6S + L146 G + I147V | +++++ |
| E144A + L152Y + L198Q + E201 G + G6S + L146H + I147T | +++++ |
| E144A + L152Y + L198Q + E201 G + G6S + I147V | ++++++ |
| E144A + L152Y + L198Q + E201 G + G6S + L146N + I147T | ++++++ |
| E144A + L152Y + L198Q + E201 G + G6S + L146Q + I147V | ++++++ |
| E144A + L152Y + L198Q + E201 G + G6S + L146T + I147V | ++++++ |
| E144A + L152Y + L198Q + E201 G + G6S + L146D + I147V | +++++ |
| E144A + L152Y + L198Q + E201 G + G6S + I147T | +++++ |
| E144A + L152Y + L198Q + E201 G + G6S + L146W + I147V | ++++++ |
| E144A + L152Y + L198Q + E201 G + G6S + L146W + I147C | ++++ |
| E144A + L152Y + L198Q + E201 G + G6S + L146M + I147A | ++++++ |
| E144A + L152Y + L198Q + E201 G + G6S + L146M + I147S | +++++ |
| E144A + L152Y + L198Q + E201 G + G6S + L146S + I147V | ++++++ |
| E144A + L152Y + L198Q + E201 G + G6S + L146I + I147A | +++++ |
| E144A + L152Y + L198Q + E201 G + G6S + L146I + I147D | +++++ |
| E144A + L152Y + L198Q + E201 G + G6S + L146A + I147V | ++++++ |
| E144A + L152Y + L198Q + E201 G + G6S + L146M + I147V | ++++++ |
| E144A + L152F + L198Q + E201 G + G6S + G148 G + D149V | ++++++ |
| E144A + L152Y + L198Q + E201 G + G6S + L146M + I147V + D42E | ++++++ |
| E144A + L152Y + L198Q + E201 G + G6S + L146M + I147V + D149I | ++++++ |
| E144A + L152Y + L198Q + E201 G + G6S + L146M + I147V + M151R | ++++++ |
| E144A + L152Y + L198Q + E201 G + G6S + L146M + I147V + D42E + T199V + K200R | ++++++ |
| E144A + L152Y + L198Q + E201 G + G6S + L146M + I147V + D42E + T199V | ++++++ |
| E144A + L152Y + L198Q + E201 G + G6S + L146M + I147V + D42E + T199V + Q76L | ++++++ |
| E144A + L152Y + L198Q + E201 G + G6S + L146M + I147V + D42E + T199V + G177D | ++++++ |
| E144A + L152Y + L198Q + E201G + G6S + L146M + I147V + D42E + T199V + S96N + I113F | ++++++ |
| E144A + L152Y + L198Q + E201G + G6S + L146M + I147V + D42E + T199V + N156S + K237E | ++++++ |
| E144A + L152Y + L198Q + E201G + G6S + L146M + I147V + D42E + T199V + F165Y + K200H | ++++++ |
| E144A + L152Y + L198Q + E201G + G6S + L146M + I147V + D42E + T199V + S96N + N156S | ++++++ |
| E144A + L152Y + L198Q + E201 G + G6S + L146M + I147V + D42E + T199V + K200H | ++++++ |
| E144A + L152Y + L198Q + E201G + G6S + L146M + I147V + D42E + T199V + K61E + N156S | ++++++ |
| E144A + L152Y + L198Q + E201G + G6S + L146M + I147V + D42E + T199V + A21V + A58T + S96N | ++++++ |
| E144A + L152Y + L198Q + E201G + G6S + L146M + I147V + D42E + T199V + G177D + A203V | ++++++ |
| E144A + L152Y + L198Q + E201 G + G6S + L146M + I147V + D42E + T199V + A87V | ++++++ |
| E144A + L152Y + L198Q + E201G + G6S + L146M + I147V + D42E + T199V + M146K + Y230F | ++++++ |

The activity was denoted by a multiple improved relative to a parent, + denoted 1-5 times of improvement, ++ denoted 5-10 times of improvement, +++ denoted 10-50 times of improvement; ++++ denoted 50-100 times of improvement; +++++ denoted 100-1000 times of improvement; and ++++++ denoted more than 1000 times of improvement.

Example 4

Mutant E144A+L152Y+L198Q+E201G+G6S+L146M+I147V+D42E+T199V+G177D+A203V were subjected to reaction for verification at different pH values, and results were shown in Table 4.

1) 2 g substrate, 2,6-dichloro-3-fluoroacetophenone, 0.1 M citric acid buffer (pH=5.0), 2 g isopropanol, 20 mg $NAD^+$, and 0.2 g ketoreductase mutant were added to a 25 mL reaction flask, and mixed evenly, and subjected to reaction for 16 h in a shaker at 30° C. and 200 rpm with a total volume of 10 mL;
2) 2 g substrate, 2,6-dichloro-3-fluoroacetophenone, 0.1 M PB (pH=6.0), 2 g isopropanol, 20 mg $NAD^+$, and 0.2 g ketoreductase mutant were added to a 25 mL reaction flask, and mixed evenly, and subjected to reaction for 16 h in a shaker at 30° C. and 200 rpm with a total volume of 10 mL;
3) 2 g substrate, 2,6-dichloro-3-fluoroacetophenone, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 30° C. and 200 rpm with a total volume of 10 mL;
4) 2 g substrate, 2,6-dichloro-3-fluoroacetophenone, 0.1 M PB (pH=8.0), 2 g isopropanol, 20 mg $NAD^+$, and 0.2 g ketoreductase mutant were added to a 25 mL reaction flask, and mixed evenly, and subjected to reaction for 16 h in a shaker at 30° C. and 200 rpm with a total volume of 10 mL.
5) 2 g substrate, 2,6-dichloro-3-fluoroacetophenone, 0.1 M Tric-HCl buffer solution (pH=9.0), 2 g isopropanol, 20 mg $NAD^+$, and 0.2 g ketoreductase mutant were added to a 25 mL reaction flask, and mixed evenly, and subjected to reaction for 16 h in a shaker at 30° C. and 200 rpm with a total volume of 10 mL.

The sampling method was the same: 0.2 mL was sampled from the sample reaction system and added to 1 mL acetonitrile, after being mixed evenly, the reaction system was put to a 2 mL EP tube and centrifuged for 3 min at 12000 rpm. Supernatant was taken to a sample sending bottle, and was subjected to HPLC detection, and the detection wavelength was 210 nm;

Detection method for ee value: 1 mL was sampled and added to 2 mL ethyl acetate, and vibrated and mixed evenly, and centrifuged for 3 min at 12000 rpm; 100 μL supernatant was taken and added to 1 mL ethyl acetate, sodium sulfate was added for drying, after vibrated and mixed evenly, the obtained product was centrifuged for 3 min at 12000 rpm; supernatant was taken, and subjected to GC detection and through a chromatographic column CYCLOSIL-B; warming program was: the temperature started to rise at 120° C. and reached to 220° C. at a rate of 15° C./min for preservation for 2 min;

TABLE 4

| No. | pH value | Conversion rate (%) | ee |
| --- | --- | --- | --- |
| 1 | 5 | 95.1 | >99% |
| 2 | 6 | >99 | >99% |
| 3 | 7 | >99 | >99% |
| 4 | 8 | >99 | >99% |
| 5 | 9 | 93.2 | >99% |

Example 5

Mutants E144A+L152Y+L198Q+E201G+G6S+L146M+I147V+D42E+T199V+G177D+A203V were subjected to reaction for verification at different temperature, and results were shown in Table 5.

1) 2 g substrate, 2,6-dichloro-3-fluoroacetophenone, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 4° C. and 200 rpm with a total volume of 10 mL;
2) 2 g substrate, 2,6-dichloro-3-fluoroacetophenone, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 10° C. and 200 rpm with a total volume of 10 mL;
3) 2 g substrate, 2,6-dichloro-3-fluoroacetophenone, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 20° C. and 200 rpm with a total volume of 10 mL;
4) 2 g substrate, 2,6-dichloro-3-fluoroacetophenone, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 30° C. and 200 rpm with a total volume of 10 mL;
5) 2 g substrate, 2,6-dichloro-3-fluoroacetophenone, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 40° C. and 200 rpm with a total volume of 10 mL;
6) 2 g substrate, 2,6-dichloro-3-fluoroacetophenone, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 50° C. and 200 rpm with a total volume of 10 mL;
7) 2 g substrate, 2,6-dichloro-3-fluoroacetophenone, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 60° C. and 200 rpm with a total volume of 10 mL;

Sampling method: 0.2 mL was sampled from the sample reaction system and added to 1 mL acetonitrile, after being mixed evenly, the sample reaction system was put to a 2 mL EP tube and centrifuged for 3 min at 12000 rpm. Supernatant was taken to a sample sending bottle, and was subjected to HPLC detection, and the detection wavelength was 210 nm;

Detection method for ee value: 1 mL was sampled and added to 2 mL ethyl acetate, and vibrated and mixed evenly, and centrifuged for 3 min at 12000 rpm; 100 μL supernatant was taken and added to 1 mL ethyl acetate, sodium sulfate was added for drying, after vibrated and mixed evenly, the obtained product was centrifuged for 3 min at 12000 rpm; supernatant was taken, and subjected to GC detection and put through a chromatographic column CYCLOSIL-B; heating-up program was: the temperature started to rise at 120° C. and reached to 220° C. at a rate of 15° C./min for preservation for 2 min;

TABLE 5

| No. | Temperature (° C.) | Conversion rate (%) | ee |
|---|---|---|---|
| 1 | 4 | 85.7 | >99% |
| 2 | 10 | 97.2 | >99% |
| 3 | 20 | >99 | >99% |
| 4 | 30 | >99 | >99% |
| 5 | 40 | >99 | >99% |
| 6 | 50 | >99 | >99% |
| 7 | 60 | 86.3 | >99% |

Example 6

A yield of mutants E144A+L152Y+L198Q+E201G+G6S+L146M+I147V+D42E+T199V+G177D+A203V was obtained and specific steps were as follows:

20 g substrate, 2,6-dichloro-3-fluoroacetophenone, 0.1 M PB (pH=7.0), 20 g isopropanol, 200 mg $NAD^+$, and 2 g ketoreductase mutant were added to a 250 mL reaction flask, and mixed evenly, and subjected to reaction for 16 h in a shaker at 30° C. and 200 rpm with a total volume of 100 mL;

0.2 mL was sampled from the sample reaction system and added to 1 mL acetonitrile, after being mixed evenly, the sample reaction system was put to a 2 mL EP tube and centrifuged for 3 min at 12000 rpm. Supernatant was taken to a sample sending bottle, and was subjected to HPLC detection, and the detection wavelength was 210 nm;

At the end of the reaction, 100 mL ethyl acetate was added for extracting for 3 times, extracted organic phases were blended and magnesium sulfate was added for drying, subjected to rotary evaporation to dry, and weighed; the product weight was 17.4 g, purity was 97%, and ee value was greater than 99%.

Example 7

Mutants E144A+L152Y+L198Q+E201G+G6S+L146M+I147V+D42E+T199V+G177D+A203V were subjected to reaction for verification under different substrates, and results were shown in Table 6.

1) 2 g substrate, 2-chloroacetophenone, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 30° C. and 200 rpm with a total volume of 10 mL;
2) 2 g substrate, 3-fluoroacetophenone, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 30° C. and 200 rpm with a total volume of 10 mL;
3) 2 g substrate, 4-methoxyacetophenone, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 30° C. and 200 rpm with a total volume of 10 mL;
4) 2 g substrate, ethyl acetoacetate, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 30° C. and 200 rpm with a total volume of 10 mL;

TABLE 6

| No. | Substrate | Conversion rate (%) | ee |
|---|---|---|---|
| 1 | 2-chloroacetophenone | 99 | >99% |
| 2 | 3-fluoroacetophenone | 99 | >99% |
| 3 | 4-methoxyacetophenone | 99 | >99% |
| 4 | Ethyl acetoacetate | 99 | >99% |

Example 8

Different mutants were used to verify the activity of 2,4-dichloroacetophenone; and results were shown in Table 7.

2 g substrate, 2-chloroacetophenone, 0.1 M PB (pH=7.0), 2 g isopropanol, 20 mg $NAD^+$, and 0.2 g ketoreductase mutant were added to a 25 mL reaction flask, and mixed evenly, and subjected to reaction for 16 h in a shaker at 30° C. and 200 rpm with a total volume of 10 mL;

TABLE 7

| No. | Mutant | Conversion rate (%) | ee |
|---|---|---|---|
| 1 | WT | 41 | >99% |
| 2 | E144A | 83 | >99% |
| 3 | L152F | 97 | >99% |
| 4 | L152R | 97 | >99% |
| 5 | L152A | 97 | >99% |
| 6 | L152V | 97 | >99% |
| 7 | E201A | 90 | >99% |
| 8 | D202A | 84 | >99% |
| 9 | E144A + L152F | 98 | >99% |
| 10 | E144A + L152F + A94Y + S96E | 98 | >99% |
| 11 | E144A + L152Y + L198Q + E201G + G6S | 98 | >99% |
| 12 | E144A + L152Y + L198Q + E201G + G6S + L146M + I147A | 98 | >99% |
| 13 | E144A + L152Y + L198Q + E201G + G6S + L146M + I147V + D42E + T199V + K200R | 98 | >99% |
| 14 | E144A + L152Y + L198Q + E201G + G6S + L146M + I147V + D42E + T199V + A21V + A58T + S96N | 98 | >99% |
| 15 | E144A + L152Y + L198Q + E201G + G6S + L146M + I147V + D42E + T199V + G177D + A203V | 98 | >99% |

The mentioned above are preferred examples of the present disclosure, and are not construed as limiting the present disclosure. A person skilled in the art knows that the present disclosure may have various amendments and variations. Any modification, equivalent replacement, improvement and the like made within the spirit and principle of the present disclosure shall fall within the protection scope of the present disclosure.

```
                    Sequence Listing

<110>   Asymchem (Tianjin) Corporation Limited

<120>   Ketoreductase Mutant and Method for Producing Chiral Alcohol

<130>   PN107290KLY

<160>   1

<170>   Patentin version 3.5

<210>   1

<211>   253

<212>   PRT

<213>   Acetobacter pasteurianus 386B

<400>   1

Met Ala Arg Val Ala Gly Lys Val Ala Ile Val Ser Gly Ala Ala Asn
1               5                   10                  15

Gly Ile Gly Lys Ala Thr Ala Gln Leu Leu Ala Lys Glu Gly Ala Lys
                20                  25                  30

Val Val Ile Gly Asp Leu Lys Glu Glu Asp Gly Gln Lys Ala Val Ala
                35                  40                  45

Glu Ile Lys Ala Ala Gly Gly Glu Ala Ala Phe Val Lys Leu Asn Val
        50                  55                  60

Thr Asp Glu Ala Ala Trp Lys Ala Ala Ile Gly Gln Thr Leu Lys Leu
65                  70                  75                  80

Tyr Gly Arg Leu Asp Ile Ala Val Asn Asn Ala Gly Ile Ala Tyr Ser
                85                  90                  95

Gly Ser Val Glu Ser Thr Ser Leu Glu Asp Trp Arg Arg Val Gln Ser
                100                 105                 110

Ile Asn Leu Asp Gly Val Phe Leu Gly Thr Gln Val Ala Ile Glu Ala
```

```
                    115                 120                 125
Met Lys Lys Ser Gly Gly Ser Ile Val Asn Leu Ser Ser Ile Glu
    130                 135                 140
Gly Leu Ile Gly Asp Pro Met Leu Ala Ala Tyr Asn Ala Ser Lys Gly
145                 150                 155                 160
Gly Val Arg Leu Phe Thr Lys Ser Ala Ala Leu His Cys Ala Lys Ser
                165                 170                 175
Gly Tyr Lys Ile Arg Val Asn Ser Val His Pro Gly Tyr Ile Trp Thr
                180                 185                 190
Pro Met Val Ala Gly Leu Thr Lys Glu Asp Ala Ala Arg Gln Lys
            195                 200                 205
Leu Val Asp Leu His Pro Ile Gly His Leu Gly Glu Pro Asn Asp Ile
            210                 215                 220
Ala Tyr Gly Ile Leu Tyr Leu Ala Ser Asp Glu Ser Lys Phe Val Thr
225                 230                 235                 240
Gly Ser Glu Leu Val Ile Asp Gly Gly Tyr Thr Ala Gln
                245                 250
```

SEQUENCE LISTING

<160> NUMBER OF SEQ ID NOS: 1

<210> SEQ ID NO 1
<211> LENGTH: 253
<212> TYPE: PRT
<213> ORGANISM: Acetobacter pasteurianus 386B

<400> SEQUENCE: 1

```
Met Ala Arg Val Ala Gly Lys Val Ala Ile Val Ser Gly Ala Ala Asn
1               5                   10                  15
Gly Ile Gly Lys Ala Thr Ala Gln Leu Leu Ala Lys Glu Gly Ala Lys
                20                  25                  30
Val Val Ile Gly Asp Leu Lys Glu Glu Asp Gly Gln Lys Ala Val Ala
                35                  40                  45
Glu Ile Lys Ala Ala Gly Gly Glu Ala Ala Phe Val Lys Leu Asn Val
                50                  55                  60
Thr Asp Glu Ala Ala Trp Lys Ala Ala Ile Gly Gln Thr Leu Lys Leu
65                  70                  75                  80
Tyr Gly Arg Leu Asp Ile Ala Val Asn Asn Ala Gly Ile Ala Tyr Ser
                85                  90                  95
Gly Ser Val Glu Ser Thr Ser Leu Glu Asp Trp Arg Val Gln Ser
                100                 105                 110
Ile Asn Leu Asp Gly Val Phe Leu Gly Thr Gln Val Ala Ile Glu Ala
                115                 120                 125
Met Lys Lys Ser Gly Gly Ser Ile Val Asn Leu Ser Ser Ile Glu
                130                 135                 140
Gly Leu Ile Gly Asp Pro Met Leu Ala Ala Tyr Asn Ala Ser Lys Gly
145                 150                 155                 160
Gly Val Arg Leu Phe Thr Lys Ser Ala Ala Leu His Cys Ala Lys Ser
                165                 170                 175
Gly Tyr Lys Ile Arg Val Asn Ser Val His Pro Gly Tyr Ile Trp Thr
                180                 185                 190
```

```
Pro Met Val Ala Gly Leu Thr Lys Glu Asp Ala Ala Ala Arg Gln Lys
        195                 200                 205

Leu Val Asp Leu His Pro Ile Gly His Leu Gly Glu Pro Asn Asp Ile
    210                 215                 220

Ala Tyr Gly Ile Leu Tyr Leu Ala Ser Asp Glu Ser Lys Phe Val Thr
225                 230                 235                 240

Gly Ser Glu Leu Val Ile Asp Gly Gly Tyr Thr Ala Gln
                245                 250
```

What is claimed is:

1. A ketoreductase mutant, wherein the amino acid sequence of the ketoreductase mutant is an amino acid sequence obtained by mutation occurred in the amino acid sequence as shown in SEQ ID NO: 1, and the amino acid mutation comprises E144A.

2. The ketoreductase mutant as claimed in claim 1, wherein the amino acid mutation further comprises L152F or L152Y.

3. The ketoreductase mutant as claimed in claim 2, wherein the amino acid mutation comprises any one of the following mutation site combinations:

E144A+L152F+A94E+S96M, E144A+L152F+A94S+S96Q, E144A+L152F+A94V, E144A+L152F+A94Y+S96E, E144A+L152F+A94S+S96N, E144A+L152F+A94S+S96R, E144A+L152F+A94A+S96E, E144A+L152F+A94Y+S96K, E144A+L152F+A94R+S96K, E144A+L152F+A94S+S96A, E144A+L152F+A94V+S96Q, E144A+L152F+A94A+S96G, E144A+L152F+A94S+S96T, E144A+L152F+S96E, E144A+L152F+A94Y+S96L, E144A+L152F+S96D, E144A+L152F+A94E+S96A, E144A+L152F+A94T+S96Y, E144A+L152F+A94S, E144A+L152F+A94E+S96C, E144A+L152F+L198V, E144A+L152F+L198V+E201C, E144A+L152F+L198I+E201I, E144A+L152F+L198V+E201A, E144A+L152F+L198V+E201N, E144A+L152F+L198V+E201L, E144A+L152F+L198Q+E201G, E144A+L152F+L198V+E201S, E144A+L152F+L198H+E201G, E144A+L152F+L198I+E201V, E144A+L152F+L198V+E201G, E144A+L152F+L198Y+E201L, E144A+L152F+L198V+E201F, E144A+L152F+L198S+E201Y, E144A+L152F+G6S, E144A+L152F+R108H, E144A+L152F+G117S, E144A+L152F+I223V, E144A+L152F+G6S+R108H, E144A+L152F+G117S+G6S, E144A+L152F+G117S+I223V, E144A+L152F+I223V+G6S, E144A+L152F+I223V+R108H, E144A+L152F+R108H+G117S, E144A+L152F+G117S+G6S, E144A+L152F+G117S+I223V+G6S, E144A+L152F+G117S+I223V+R108H, E144A+L152F+L198Q+E201G+G6S, E144A+F152Y+G6S, E144A+L152Y+L198Q+E201G, E144A+L152Y+L198Q+E201G+G6S, E144A+L152Y+L198Q+E201G+G6S+L146V+I147A, E144A+L152Y+L198Q+E201G+G6S+L146Q+I147R, E144A+L152Y+L198Q+E201G+G6S+L146L+I147L, E144A+L152Y+L198Q+E201G+G6S+L146V+I147T, E144A+L152Y+L198Q+E201G+G6S+L146C+I147V, E144A+L152Y+L198Q+E201G+G6S+L146I+I147R, E144A+L152Y+L198Q+E201G+G6S+L146G+I147V, E144A+L152Y+L198Q+E201G+G6S+L146L+I147V, E144A+L152Y+L198Q+E201G+G6S+L146L+I147R, E144A+L152Y+L198Q+E201G+G6S+L146H+I147T, E144A+L152Y+L198Q+E201G+G6S+L146L+I147V, E144A+L152Y+L198Q+E201G+G6S+L146N+I147T, E144A+L152Y+L198Q+E201G+G6S+L146Q+I147V, E144A+L152Y+L198Q+E201G+G6S+L146T+I147V, E144A+L152Y+L198Q+E201G+G6S+L146D+I147V, E144A+L152Y+L198Q+E201G+G6S+L146L+I147T, E144A+L152Y+L198Q+E201G+G6S+L146W+I147V, E144A+L152Y+L198Q+E201G+G6S+L146W+I147C, E144A+L152Y+L198Q+E201G+G6S+L146M+I147A, E144A+L152Y+L198Q+E201G+G6S+L146M+I147S, E144A+L152Y+L198Q+E201G+G6S+L146S+I147V, E144A+L152Y+L198Q+E201G+G6S+L146I+I147A, E144A+L152Y+L198Q+E201G+G6S+L146I+I147D, E144A+L152Y+L198Q+E201G+G6S+L146A+I147V, E144A+L152Y+L198Q+E201G+G6S+L146M+I147V, E144A+L152F+L198Q+E201G+G6S+G148G+D149V, E144A+L152Y+L198Q+E201G+G6S+L146M+I147V+D42E, E144A+L152Y+L198Q+E201G+G6S+L146M+I147V+D149I, E144A+L152Y+L198Q+E201G+G6S+L146M+I147V+M151R, E144A+L152Y+L198Q+E201G+G6S+L146M+I147V+D42E+T199V+K200R, E144A+L152Y+L198Q+E201G+G6S+L146M+I147V+D42E+T199V, E144A+L152Y+L198Q+E201G+G6S+L146M+I147V+D42E+T199V+Q76L, E144A+L152Y+L198Q+E201G+G6S+L146M+I147V+D42E+T199V+G177D, E144A+L152Y+L198Q+E201G+G6S+L146M+I147V+D42E+T199V+S96N+I113F, E144A+L152Y+L198Q+E201G+G6S+L146M+I147V+D42E+T199V+N156S+K237E, E144A+L152Y+L198Q+E201G+G6S+L146M+I147V+D42E+T199V+F165Y+K200H, E144A+L152Y+L198Q+E201G+G6S+L146M+I147V+D42E+T199V+S96N+N156S, E144A+L152Y+L198Q+E201G+G6S+L146M+I147V+D42E+T199V+K200H, E144A+L152Y+L198Q+E201G+G6S+L146M+I147V+D42E+T199V+K61E+N156S, E144A+L152Y+L198Q+E201G+G6S+L146M+I147V+D42E+T199V+A21V+A58T+S96N, E144A+L152Y+L198Q+E201G+G6S+L146M+I147V+D42E+T199V+G177D+A203V, E144A+L152Y+L198Q+E201G+G6S+L146M+I147V+D42E+T199V+A87V and E144A+L152Y+L198Q+E201G+G6S+L146M+I147V+D42E+T199V+M146K+Y230F.

4. The ketoreductase mutant as claimed in claim 1, wherein the amino acid mutation comprises any one of the following mutation site combinations: E144A+L152R, E144A+L152A, E144A+L152V, E144A+E201A, E144A+D202A, E144A+L152W, E144A+L152M, E144A+L152L, E144A+L152K, E144A+L152T, E144A+L152P, E144A+L152C, E144A+L152H, E144A+L152Q, E144A+L152E, E144A+L152S, E144A+L152G, E144A+F152C+G6S, E144A+L152C+L198Q+E201G and E144A+L152C+L198Q+E201G+G6S.

5. A DNA molecule, wherein the DNA molecule encodes the ketoreductase mutant as claimed in claim 1.

6. A recombinant plasmid, wherein the recombinant plasmid comprises the DNA molecule as claimed in claim 5.

7. The recombinant plasmid as claimed in claim 6, wherein the recombinant plasmid is pET-22a(+), pET-22b (+), pET-3a(+), pET-3d(+), pET-11a(+), pET-12a(+), pET-14b(+), pET-15b(+), pET-16b(+), pET-17b(+), pET-19b(+), pET-20b(+), pET-21a(+), pET-23a(+), pET-23b(+), pET-24a (+), pET-25b(+), pET-26b(+), pET-27b(+), pET-28a(+), pET-29a(+), pET-30a(+), pET-31b(+), pET-32a(+), pET-35b (+), pET-38b(+), pET-39b(+), pET-40b(+), pET-41a(+), pET-41b(+), pET-42a(+), pET-43a(+), pET-43b(+), pET-44a (+), pET-49b(+), pQE2, pQE9, pQE30, pQE31, pQE32, pQE40, pQE70, pQE80, pRSET-A, pRSET-B, pRSET-C, pGEX-5X-1, pGEX-6p-1, pGEX-6p-2, pBV220, pBV221, pBV222, pTrc99A, pTwin1, pEZZ18, pKK232-18, pUC-18 or pUC-19.

8. A host cell, wherein the host cell comprises the recombinant plasmid as claimed in claim 6.

9. The host cell as claimed in claim 8, wherein the host cell comprises a prokaryotic cell or a eukaryotic cell.

10. The host cell as claimed in claim 9, wherein the prokaryotic cell is *Escherichia coli*.

11. A method for producing chiral alcohol, comprising a step of performing a reduction reaction on a chiral ketones compound to produce the chiral alcohol catalyzed by ketoreductase, wherein the ketoreductase is the ketoreductase mutant as claimed in claim 1.

12. The method as claimed in claim 11, wherein the chiral ketone compound has the following structural formula

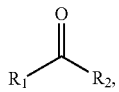

wherein $R_1$ and $R_2$ respectively independently are alkyl, cycloalkyl, aryl or heteroaryl, or the $R_1$ and the $R_2$ form a heterocyclyl, a carbocycle group or the heteroaryl with carbon on a carbonyl together, a heteroatom in the heterocyclyl and the heteroaryl is respectively independently selected from at least one of nitrogen, oxygen and sulfur, an aryl in the aryl, a heteroaryl in the heteroaryl, a carbocycle group in the carbocycle group or a heterocyclyl in the heterocyclyl are respectively independently unsubstituted or substituted by at least one group of halogen, alkoxy or alkyl;

the $R_1$ and the $R_2$ respectively and independently are $C_1$-$C_8$ alkyl, $C_5$-$C_{10}$ cycloalkyl, $C_5$-$C_{10}$ aryl or $C_5$-$C_{10}$ heteroaryl, or the $R_1$ and the $R_2$ form a $C_5$-$C_{10}$ heterocyclyl, a $C_5$-$C_{10}$ carbocycle group or the $C_5$-$C_{10}$ heteroaryl with the carbon on the carbonyl together, a heteroatom in the $C_5$-$C_{10}$ heterocyclyl and the $C_5$-$C_{10}$ heteroaryl is respectively independently selected from at least one of nitrogen, oxygen or sulfur, an aryl in the $C_5$-$C_{10}$ aryl, a heteroaryl in the $C_5$-$C_{10}$ heteroaryl, a carbocycle group in the $C_5$-$C_{10}$ carbocycle group or a heterocyclyl in the $C_5$-$C_{10}$ heterocyclyl are respectively independently unsubstituted or substituted by at least one group of halogen, alkoxy or alkyl.

13. The method as claimed in claim 12, wherein a structure of the ketones compound is

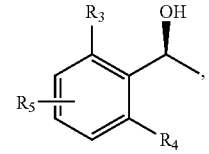

wherein $R_3$ is H, F, Cl, Br or $CH_3$, $R_4$ is H, F, Cl, Br or $CH_3$, and $R_5$ is H, F, Cl, Br, $CH_3$, $OCH_3$ or $CH_2CH_3$.

14. The method as claimed in claim 13, wherein the ketones compound is

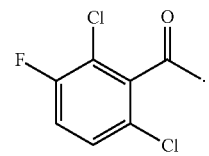

15. The method as claimed in claim 11, wherein a reaction system for performing the reduction reaction on the ketones compound to produce the chiral alcohol catalyzed by the ketoreductase further comprises coenzyme, a coenzyme regeneration system and buffer.

16. The method as claimed in claim 15, wherein in the reaction system, a concentration of the ketones compound is 1 g/L-200 g/L.

17. The method as claimed in claim 15, wherein a pH value of the reaction system is 5-9, and a reaction temperature of the reaction system is 4-60 DEG C.

18. The method as claimed in claim 15, wherein the buffer is phosphate buffer, Tris-hydrochloric acid buffer, barbital sodium-hydrochloric acid buffer or citric acid-sodium citrate buffer.

19. The method as claimed in claim 15, wherein the coenzyme is NADH.

20. The method as claimed in claim 19, wherein the coenzyme regeneration system comprises: isopropanol, coenzyme $NAD^+$ and the ketoreductase.

* * * * *